United States Patent
Neumann

(10) Patent No.: US 11,967,401 B2
(45) Date of Patent: Apr. 23, 2024

(54) METHODS AND SYSTEMS FOR PHYSIOLOGICALLY INFORMED NETWORK SEARCHING

(71) Applicant: KPN Innovations, LLC, Lakewood, CO (US)

(72) Inventor: Kenneth Neumann, Lakewood, CO (US)

(73) Assignee: KPN Innovations, LLC, Lakewood, CO (US)

(*) Notice: Subject to any disclaimer, the term of this patent is extended or adjusted under 35 U.S.C. 154(b) by 0 days.

(21) Appl. No.: 16/727,113

(22) Filed: Dec. 26, 2019

(65) Prior Publication Data

US 2021/0202045 A1 Jul. 1, 2021

(51) Int. Cl.

| | |
|---|---|
| G16B 50/30 | (2019.01) |
| G06F 16/951 | (2019.01) |
| G06F 16/953 | (2019.01) |
| G06F 18/214 | (2023.01) |
| G06F 18/23213 | (2023.01) |
| G06F 18/241 | (2023.01) |
| G06K 9/62 | (2022.01) |
| G06N 20/00 | (2019.01) |
| G16B 40/20 | (2019.01) |

(52) U.S. Cl.
CPC ........... *G16B 50/30* (2019.02); *G06F 16/951* (2019.01); *G06F 16/953* (2019.01); *G06F 18/214* (2023.01); *G06F 18/23213* (2023.01); *G06F 18/241* (2023.01); *G06N 20/00* (2019.01)

(58) Field of Classification Search
CPC ..... G06F 17/953; G06F 16/951; G06N 20/00; G16B 40/20; G06K 9/6223

USPC ......................................................... 707/705
See application file for complete search history.

(56) References Cited

U.S. PATENT DOCUMENTS

| | | | |
|---|---|---|---|
| 9,424,532 B1 | 8/2016 | Abedini et al. | |
| 10,365,716 B2* | 7/2019 | Aimone | G09G 3/003 |
| 10,489,474 B1 | 11/2019 | Tang et al. | |
| 2007/0172155 A1* | 7/2007 | Guckenberger | G06F 16/583 |
| | | | 707/E17.02 |
| 2013/0222388 A1* | 8/2013 | McDonald | G06F 16/9024 |
| | | | 345/440 |
| 2016/0042035 A1* | 2/2016 | Ajmera | G06F 16/951 |
| | | | 707/722 |

(Continued)

OTHER PUBLICATIONS

Richard Waters, Google Uses AI to Boost Search Engine Ranking Efficiency, Financial Times, Oct. 25, 2019, San Francisco.

*Primary Examiner* — Son T Hoang
*Assistant Examiner* — Earl Levi Elias
(74) *Attorney, Agent, or Firm* — Caldwell Intellectual Property Law

(57) ABSTRACT

In an aspect, a system for physiologically informed network searching, includes a computing device designed and configured to receive a biological extraction from a user, input the biological extraction to an index classifier, the index classifier configured to input biological extractions and output web search indices, wherein the classifier is generated by executing a classification algorithm clustering a plurality of user physiological data records to a plurality of user cohort labels, output, from the index classifier, a physiologically linked web index, receive, from the user, a search query, and generate, using the physiologically linked web index and the search query, a ranked search result.

18 Claims, 5 Drawing Sheets

(56) References Cited

U.S. PATENT DOCUMENTS

| | | | |
|---|---|---|---|
| 2016/0055243 A1* | 2/2016 | Xu .................... | G06F 16/9538 |
| | | | 707/709 |
| 2017/0155631 A1 | 6/2017 | Du | |
| 2018/0124459 A1* | 5/2018 | Knox .................. | G06V 40/174 |
| 2018/0349478 A1 | 12/2018 | Carlisle et al. | |
| 2019/0027232 A1 | 1/2019 | Beim et al. | |
| 2019/0130309 A1* | 5/2019 | Jiang .................... | G06F 16/906 |
| 2019/0172584 A1* | 6/2019 | Athey ................... | G16H 10/60 |
| 2019/0244541 A1 | 8/2019 | Hadad et al. | |
| 2019/0295440 A1 | 9/2019 | Hadad | |
| 2019/0304000 A1* | 10/2019 | Simpson ............... | G01N 33/492 |
| 2019/0304604 A1 | 10/2019 | Kupersmith et al. | |
| 2019/0318044 A1 | 10/2019 | Leka | |
| 2020/0160998 A1* | 5/2020 | Ward ................. | G06F 18/2185 |

* cited by examiner

METHODS AND SYSTEMS FOR PHYSIOLOGICALLY INFORMED NETWORK SEARCHING

FIELD OF THE INVENTION

The present invention generally relates to the field of artificial intelligence. In particular, the present invention is directed to methods and systems for physiologically informed network searching.

BACKGROUND

Internet search algorithms are generally designed to provide search results ranked according to general ranking criteria. Unfortunately, such criteria can sometimes be suboptimal for a particular user.

SUMMARY OF THE DISCLOSURE

In an aspect, a system for physiologically informed network searching, includes a computing device designed and configured to receive a biological extraction from a user, input the biological extraction to an index classifier, the index classifier configured to input biological extractions and output web search indices, wherein the classifier is generated by executing a classification algorithm clustering a plurality of user physiological data records to a plurality of user cohort labels, output, from the index classifier, a physiologically linked web index, receive, from the user, a search query, and generate, using the physiologically linked web index and the search query, a ranked search result.

In another aspect a method of physiologically informed network searching includes receiving, at a computing device, a biological extraction from a user. The method includes inputting, by the computing device, the biological extraction to an index classifier, the index classifier configured to input biological extractions and output web search indices, wherein the classifier is generated by executing a classification algorithm clustering a plurality of user physiological data records to a plurality of user cohort labels. The method includes outputting, by the computing device and from the index classifier, a physiologically linked web index. The method includes receiving, from the user, a search query. The method includes generating, using the physiologically linked web index and the search query, a ranked search result.

In another aspect, a non-transitory computer-readable storage medium containing machine-executable instructions for performing a method of physiologically informed network searching, the method including receiving, at a computing device, a biological extraction from a user, inputting, by the computing device, the biological extraction to an index classifier, the index classifier configured to input biological extractions and output web search indices, wherein the classifier is generated by executing a classification algorithm clustering a plurality of user physiological data records to a plurality of user cohort labels, outputting, by the computing device and from the index classifier, a physiologically linked web index, receiving, from the user, a search query, and generating, using the physiologically linked web index and the search query, a ranked search result.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Aspects of the disclosed embodiments may provide web search indices and results that are tailored to needs and/or searching patterns of physiologically similar cohorts of users. Embodiments may be self-correcting and learning, with ability to add new cohorts and attendant indices, to determine when such additions are appropriate, and to find a user's cohort index efficiently prior to operation of searches.

Figure 1:
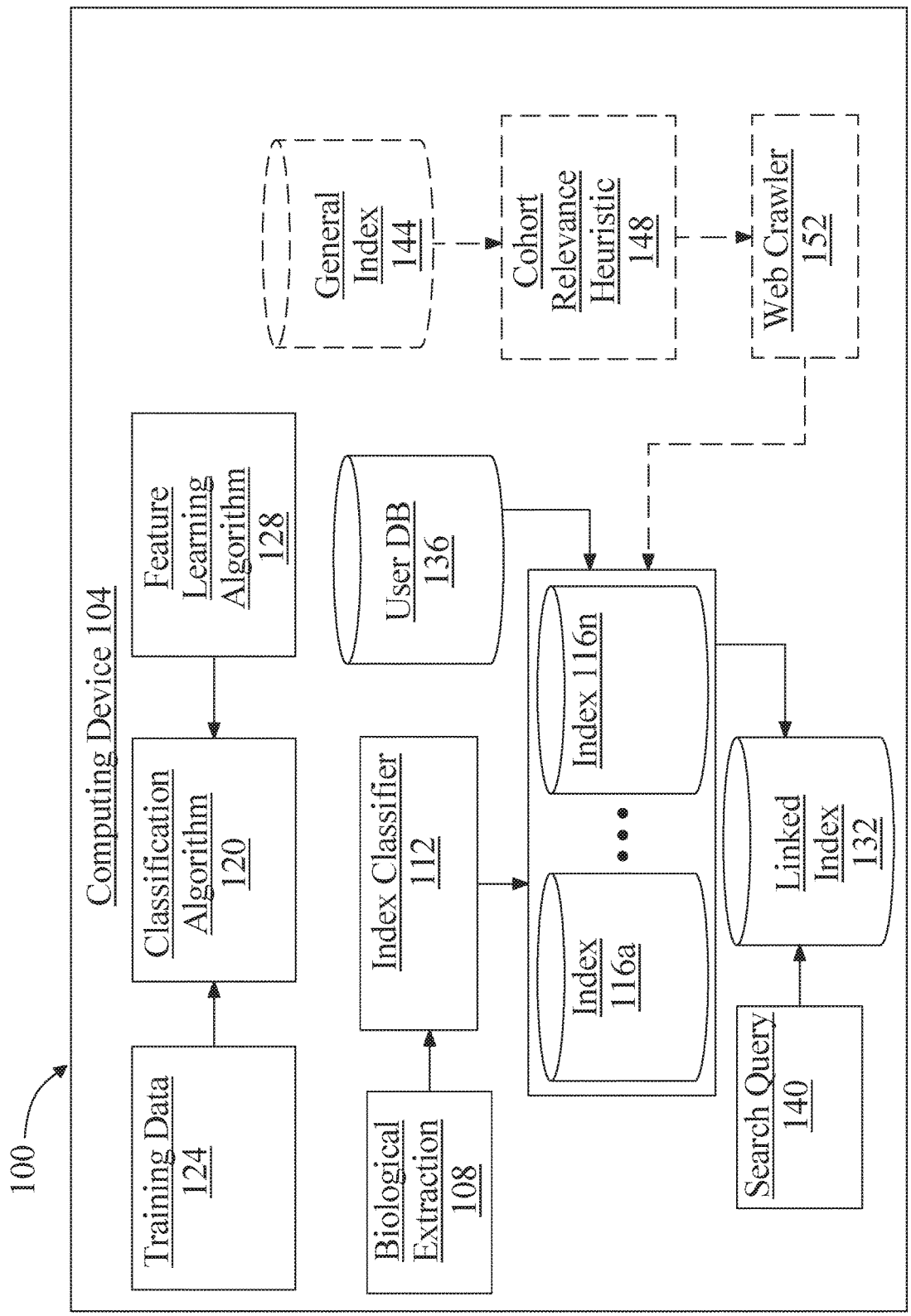
FIG. 1 is a block diagram of an exemplary embodiment of a system for physiologically informed network searching.

Referring now to FIG. 1, an exemplary embodiment of a system 100 for physiologically informed network searching is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing device 104s may be included together in a single computing device 104 or in two or more computing device 104s. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104s, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing device 104s in a first location and a second computing device 104 or cluster of computing device 104s in a second location. Computing device 104 may include one or more computing device 104s dedicated to data storage, security, distribution of traffic for load balancing, and the like. Computing device 104 may distribute one or more computing tasks as described below across a plurality of computing device 104s of computing device 104, which may operate in parallel, in series, redundantly, or in any other manner used for distribution of tasks or memory between computing device 104s. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to record a user biological extraction 108 containing an element of user physiological data. A "biological extraction 108" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR.). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels.

Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing device 104s; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface 184 object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile*, *Cryptosporidium* species, *Cyclospora cayetanensis*, *Cryptosporidium* EIA, *Dientamoeba fragilis*, *Entamoeba histolytica*, *Escherichia coli*, *Entamoeba histolytica*, *Giardia*, *H. pylori*, *Candida albicans*, *Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies*' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, Bacteroides vulgates', Bacteroides-*Prevotella*, *Barnesiella* species, *Bifidobacterium longarm*, *Bifidobacterium* species, *Butyrivbrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

Continuing to refer to FIG. 1, computing device 104 is configured to input biological extraction 108 to an index classifier 112. In an embodiment, index classifier 112 is a classifer. A "classifier," as used in this disclosure is a machine-learning model, such as a mathematical model, neural net, or program generated by a machine learning algorithm known as a "classification algorithm 120," as described in further detail below, that sorts inputs into categories or bins of data, outputting the categories or bins of data and/or labels associated therewith. Index classifier 112 is a classifier configured to input biological extractions 108 and output web search indices 116a-n, where outputting web search indices 116a-n here signifies outputting labels of web search indices 116a-n.

Still referring to FIG. 1, a "web search index," as defined in this disclosure is a data structure that stores uniform resource locators (URLs) of web pages together with one or more associated data that may be used to retrieve URLs by querying the web search index; associated data may include keywords identified in pages associated with URLs by programs such as web crawlers and/or "spiders." A web search index may include any data structure for ordered storage and retrieval of data, which may be implemented as a hardware or software module. A web search index may be implemented, without limitation, as a relational database, a key-value retrieval datastore such as a NOSQL database, or any other format or structure for use as a datastore that a person skilled in the art would recognize as suitable upon review of the entirety of this disclosure. Data entries in a a web search index may be flagged with or linked to one or more additional elements of information, which may be reflected in data entry cells and/or in linked tables such as tables related by one or more indices 116a-n in a relational database. Persons skilled in the art, upon reviewing the entirety of this disclosure, will be aware of various ways in which data entries in a web search index may reflect categories, cohorts, and/or populations of data consistently with this disclosure. In an embodiment, a web search query 140 at a search engine may be submitted as a query to a web search index, which may retrieve a list of URLs responsive to the query. In an embodiment, each web search index of plurality of web search indices 116a-n may be identified by a user cohort label, which as used in this disclosure is a label that matches a set or cluster of users having similar physiological data and/or attributes. In an embodiment, index classifier 112 is generated by executing a classification algorithm 120 clustering a plurality of user physiological data records to a plurality of user cohort labels.

Computing device 104 and/or another device may generate index classifier 112 using a classification algorithm 120, defined as a processes whereby a computing device 104 derives a classifier from training data 124. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, training data 124, as used in this disclosure, is data containing correlations that a machine-learning process may use to model relationships between two or more categories of data elements. For instance, and without limitation, training data 124 may include a plurality of data entries, each entry representing a set of data elements that were recorded, received, and/or generated together; data elements may be correlated by shared existence in a given data entry, by proximity in a given data entry, or the like. Multiple data entries in training data 124 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 124 according to various correlations; correlations may indicate causative and/or predictive links between categories of data elements, which may be modeled as relationships such as mathematical relationships by machine-learning processes as described in further detail below. Training data 124 may be formatted and/or organized by categories of data elements, for instance by associating data elements with one or more descriptors corresponding to categories of data elements. As a non-limiting example, training data 124 may include data entered in standardized forms by persons or processes, such that entry of a given data element in a given field in a form may be mapped to one or more descriptors of categories. Elements in training data 124 may be linked to descriptors of categories by tags, tokens, or other data elements; for instance, and without limitation, training data 124 may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data 124 may include one or more elements that are not categorized; that is, training data 124 may not be formatted or contain descriptors for some elements of data. Machine-learning algorithms and/or other processes may sort training data 124 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 124 to be made applicable for two or more distinct machine-learning algorithms as described in further detail below. Training data 124 used by computing device 104 may correlate any input data as described in this disclosure to any output data as described in this disclosure.

Still referring to FIG. 1, index training data 124, defined as training data 124 used to generate index classifier 112, may include, without limitation, a plurality of data entries, each data entry including one or more elements of physiological data such as biological extractions 108, and one or more correlated user cohort labels, where user cohort labels and associated physiological profiles may be identified using feature learning algorithms 128 as described below. Index training data 124 and/or elements thereof may be added to, as a non-limiting example, by classification of multiple users' physiological data to cohort labels using one or more classification algorithms 120.

Still referring to FIG. 1, computing device 104 may be configured to generate index classifier 112 using a Naïve Bayes classification algorithm 120. Naïve Bayes classification algorithm 120 generates classifiers by assigning class labels to problem instances, represented as vectors of element values. Class labels are drawn from a finite set. Naïve Bayes classification algorithm 120 may include generating a family of algorithms that assume that the value of a particular element is independent of the value of any other element, given a class variable. Naïve Bayes classification algorithm 120 may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data 124 into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm 120 may include a gaussian model that follows a normal distribution. Naïve Bayes classification algorithm 120 may include a multinomial model that is used for discrete counts. Naïve Bayes classification algorithm 120 may include a Bernoulli model that may be utilized when vectors are binary.

With continued reference to FIG. 1, computing device 104 may be configured to generate index classifier 112 using a K-nearest neighbors (KNN) algorithm. A "K-nearest neighbors algorithm" as used in this disclosure, includes a classification method that utilizes feature similarity to analyze how closely out-of-sample-features resemble training data 124 to classify input data to one or more clusters and/or categories of features as represented in training data 124; this may be performed by representing both training data 124 and input data in vector forms, and using one or more measures of vector similarity to identify classifications within training data 124, and to determine a classification of input data. K-nearest neighbors algorithm may include specifying a K-value, or a number directing the classifier to select the k most similar entries training data 124 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data 124. Heuristic may include selecting some number of highest-ranking associations and/or training data 124 elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data 124 are represented by different quantities of samples, which may result in proportionally equivalent vectors with divergent values. As a non-limiting example, K-nearest neighbors algorithm may be configured to classify an input vector including a plurality of user-entered words and/or phrases, a plurality of attributes of a media item, such as spoken or written text, objects depicted in images, metadata, or the like, to clusters representing themes.

In an embodiment, and still referring to FIG. 1, computing device 104, and/or a device generating index classifier 112, may generate new cohort labels using a feature learning algorithm 128. A "feature learning algorithm 128," as used herein, is a machine-learning algorithm that identifies associations between elements of data in a training data 124 set, where particular outputs and/or inputs are not specified. For instance, and without limitation, a feature learning algorithm 128 may detect co-occurrences of sets of physiological data, as defined above, with each other. As a non-limiting example, feature learning algorithm 128 may detect co-occurrences of gene combinations, as defined above, with each other. Computing device 104 may perform a feature learning algorithm 128 by dividing physiological data from a given person into various sub-combinations of such data to create physiological data sets as described above, and evaluate which physiological data sets tend to co-occur with which other physiological data sets; for instance, where physiological state data includes genetic sequences, computing device 104 may divide each genetic sequence into individual genes and evaluate which individual genes and/or combinations thereof tend to co-occur with which other individual genes, and/or other physiological data. In an embodiment, first feature learning algorithm 128 may perform clustering of data.

Continuing refer to FIG. 1, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device 104 may generate a k-means clustering algorithm receiving unclassified physiological state data and outputs a definite number of classified data entry clusters wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related physiological data, which may be provided with user cohort labels; this may, for instance, generate an initial set of user cohort labels from an initial set of user physiological data of a large number of users, and may also, upon subsequent iterations, identify new clusters to be provided new user cohort labels, to which additional user physiological data may be classified, or to which previously used user physiological data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on argmin $n_{c_i \ni c}$ dist($c_i$, x)$^2$, where argmin includes argument of the minimum, $c_i$ includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i| \Sigma x_i \ni S_i^{x_i}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set. Degree of similarity index value may indicate how close a particular combination of genes, negative behaviors and/or negative behavioral propensities is to being classified by k-means algorithm to a particular cluster. K-means clustering algorithm may evaluate the distances of the combination of genes, negative behaviors and/or negative behavioral propensities to the k-number of clusters output by k-means clustering algorithm. Short distances between a set of physiological data and a cluster may indicate a higher degree of similarity between the set of physiological data and a particular cluster. Longer distances between a set of physiological behavior and a cluster may indicate a lower degree of similarity between a physiological data set and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a physiological data set and the data entry cluster. Alternatively or additionally k-means clustering algorithm may select a plurality of clusters having low degree of similarity index values to physiological data sets, indicative of greater degrees of similarity. Degree of similarity index values may be compared to a threshold number indicating a minimal degree of relatedness suitable for inclusion of a set of physiological data in a cluster, where degree of similarity indices 116a-n falling under the threshold number may be included as indicative of high degrees of relatedness. The above-described illustration of feature learning using k-means clustering is included for illustrative purposes only, and should not be construed as limiting potential implementation of feature learning algorithms 128; persons skilled in the art, upon reviewing the entirety of this disclosure, will be aware of various additional or alternative feature learning approaches that may be used consistently with this disclosure.

In an embodiment, and still referring to FIG. 1, computing device 104 and/or another device in communication therewith may generate an initial set of user cohort labels using an initial feature learning algorithm 128; for instance, an initial estimate number k of user cohort labels may be created, and feature learning algorithm 128 may be performed to generate k clusters. This may be followed by performance of a classification algorithm 120; where a threshold number of physiological data sets does not converge within a threshold distance of any cluster according to the classification algorithm 120, device performing these processes may increment k by one or more integer values and perform feature learning algorithm 128 a second time; this may be repeated until a threshold proportion of population of physiological data sets converges within a threshold distance of clusters under classification algorithm 120.

Figure 2:
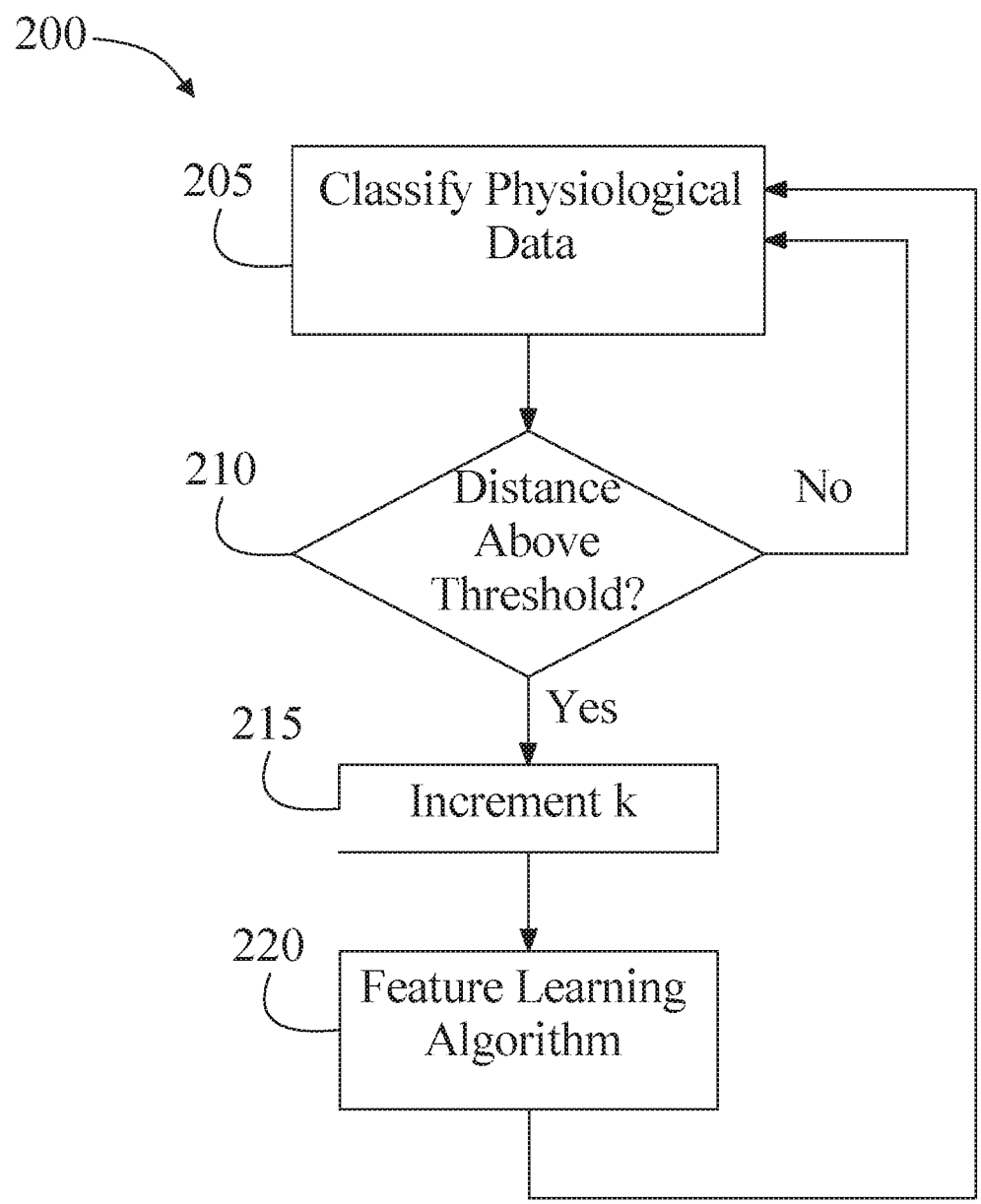
FIG. 2 is a logic flow diagram illustrating an exemplary embodiment of a process for generation of new cohort labels.

Referring to FIG. 2, computing device 104 and/or other device may follow a process 200 for creation of new cohort labels, either initially or when index classifier 112 is being run against newly submitted biological extractions 108. At step 205, computing device 104 and/or other device may perform classification of one or more elements of physiological data and/or biological extractions 108 as described above. At step 210, computing device 104 and/or other device may record degree of convergence with existing clusters of each such biological extraction 108; if distances, such as average distances from cohort label clusters, are below a threshold level, process 200 may return to classification with current cohort labels, for instance using new biological extractions 108 or the like. Where a threshold population fails to converge within a threshold distance of existing clusters, k may be incremented at step 215 and feature learning algorithm 128 may be run at step 220 to generate one or more new cohort labels, to which physiological data sets may be classified by running classification algorithm 120 to generate an updated index classifier 112. Process 200 may then return to classification 205 and repeat determinations; k may be incremented, and feature learning performed, repeatedly, until convergence brings distances below a desired and/or recorded threshold level. System 100 may ensure by such a process that classification algorithm 120 identifies cohorts closely related to a user; this may help to ensure that search results are closely tailored to a user based on biological extraction 108.

Referring again to FIG. 1, computing device 104 is configured to output, from the index classifier 112, a physiologically linked web index. Index classifier 112 may classify biological extraction 108 to a cohort label using a classification algorithm 120 as described above, for instance by identifying a cohort label associated with a cluster of physiological data sets having a greatest degree of similarity to biological extraction 108. In an embodiment, computing device 104 may include additional physiological data associated with user, such as without limitation physiological data received in past biological extractions 108 from user. Physiological data of each user may be stored, without limitation, in a user database 136, which may be implemented using any data structure suitable for implementation of web indices 116a-n; user database 136 may be located in memory of computing device 104 and/or on another device in and/or in communication with system 100.

Figure 3:
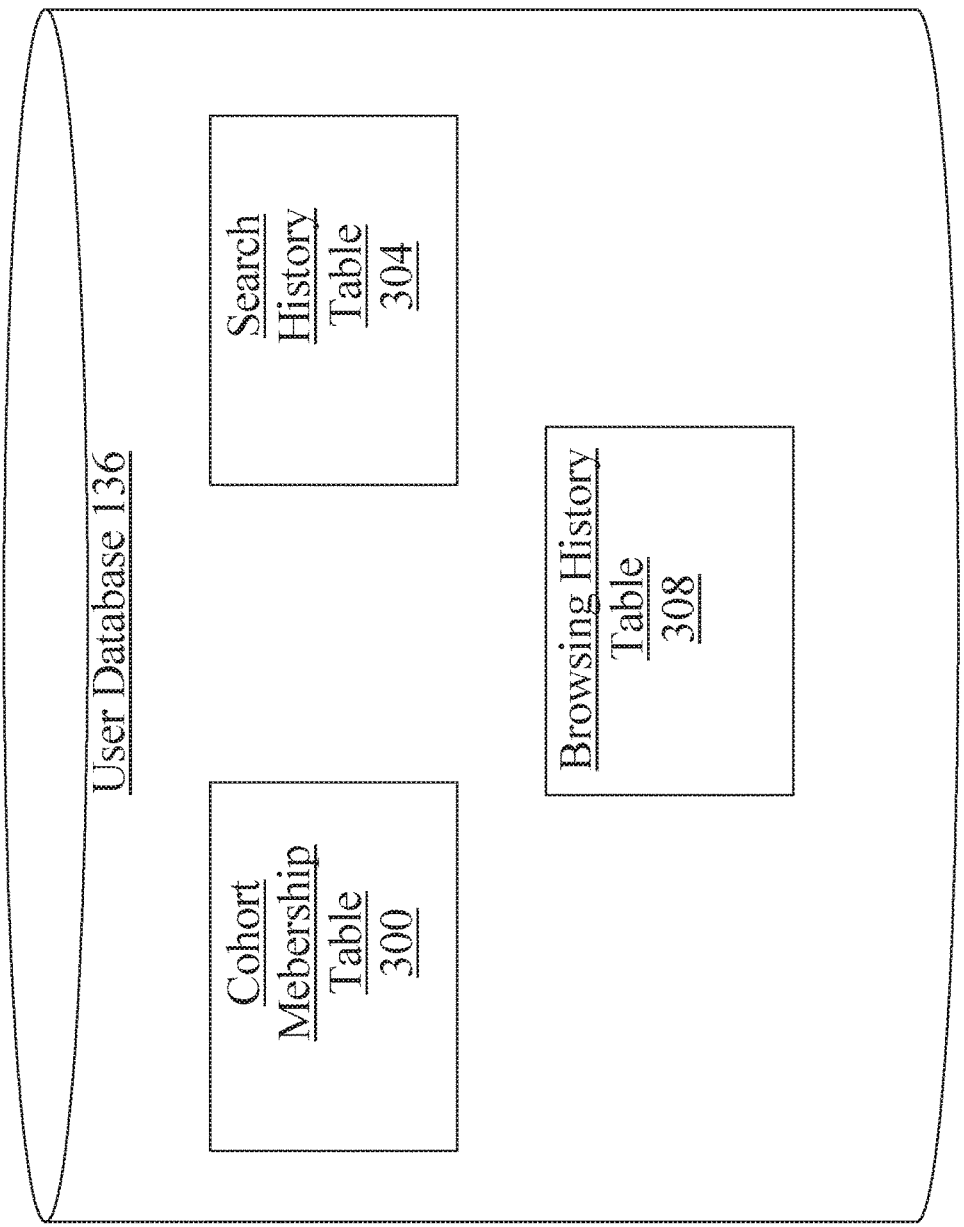
FIG. 3 is a block diagram illustrating an exemplary embodiment of a user database.

Referring now to FIG. 3, an exemplary embodiment of a user database 136 136 is illustrated. One or more tables in user database 136 136 may include, without limitation, a cohort membership table 300, which may be used to store identities of cohort labels to which users are currently classified according to biological extraction 108 classification as described above. One or more tables in user database 136 136 may include, without limitation, a search history table 304, which may be used to store history of searches; history may be recorded per user and/or per cohort. User database 136 140 may include a browsing history table 308, where history of browsing by users and/or cohorts may be recorded, for instance and without limitation for use in generation of cohort relevance heuristic 148s as described below. Persons skilled in the art, upon reviewing the entirety of this disclosure, will be aware of various alternative or additional data which may be stored in user database 136, including without limitation any data concerning any user activity, demographics, profile information, viewing and/or media consumption history, or the like.

Referring again to FIG. 1, computing device 104 is configured to receive a search query 140 from a user. Search query 140 may include a textual word and/or phrase, such as a search query 140 that a person might enter into a search engine. Computing device 104 may parse search query 140 to generate one or more keywords, where keywords may include single words and/or phrases of two or more words. Computing device 104 may, for instance, tokenize search query 140 to separate search query 140 into individual words. Computing device 104 may filter out "stop words" that do not convey meaning, such as "of," "a," "an," "the," or the like. Computing device 104 may use words parsed from search query 140 directly as keywords for retrieval from physiologically linked web index. Alternatively or additionally, computing device 104 may generate phrases to use as keywords and/or map one or more words or phrases from search query 140 to a keyword query for retrieval from physiologically linked web index using a language processing module. Language processing module may include any hardware and/or software module. Language processing module may be configured to extract, from the one or more documents, one or more words. One or more words may include, without limitation, strings of one or characters, including without limitation any sequence or sequences of letters, numbers, punctuation, diacritic marks, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module may operate to produce a language processing model. Language processing model may include a program automatically generated by computing device 104 and/or language processing module to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant.

Still referring to FIG. 1, language processing module and/or computing device 104 may generate the language processing model by any suitable method, including without limitation a natural language processing classification algorithm 120; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm 120 that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module may use a corpus of documents to generate associations between language elements in a language processing module, and language processing module and/or computing device 104 may then use such associations to analyze words extracted from one or more documents and determine relationships between such words. Corpus of documents may include any set of documents, such as a plurality of web pages, textual conversation logs, articles, blog posts, excerpts from and/or electronic texts of books or the like. Alternatively or additionally, language processing module may generate a model using correlations between words and/or phrases compiled by a third party, such as the n-grams database provided by Alphabet, Inc. of Mountain View, CA.

With continued reference to FIG. 1, search entry may be performed by offering an entry field to a user in a graphical user interface (GUI), which may be provided to a display of a user device. GUI may offer user options such as date ranges, content categories such as videos, images, general content, news, shopping, maps, and the like. GUI may provide one or more options for forms of search; for instance, GUI may provide natural language searching, which may utilize a language processing module as described above to process sentences or phrases entered by a user in a manner similar to a conversational question. GUI may provide an option to enter a Boolean search; in other words, computing device 104 may parse search query 140 for Boolean operators such as AND, OR, NOT and the like, and apply logic of such operators to search results using program commands implementing Boolean logic. GUI may be used to offer proximity search, where a distance between keywords from query in content at result URLs is used as a ranking or selection criterion thereof; alternatively or additionally, searching for an exact phrase and/or synonymous or closely related phrases may be performed using, without limitation, language processing modules and/or language processing models such as vector spaces, effectively adding proximity between keywords and/or synonyms thereof to criteria for finding and/or ranking search results.

Still referring to FIG. 1, computing device 104 is configured to generate, using the physiologically linked web index and the search query 140, a ranked search result. Search result may be retrieved from physiologically linked web index by submission of words and/or phrases as queries to physiologically linked web index; queries and results thereof may be processed in any manner suitable for queries of databases, data stores, and the like. Search result may take the form of a list of URLs returned in response to queries, for instance in the form of links to such URLs. Search result may be ranked. Entries in an index such as physiologically linked web index may have rankings associated therewith based on relevance to cohort, for instance using heuristics during crawling or index generation, as described below. A rank of an index entry may be represented by a first numerical variable, which may be referred to herein as an "index rank." Ranking may alternatively or additionally be determined according to a number of keyword and/or phrase detections in content at a give URL; for instance, a numerical variable referred to herein as a "relevance rank" may be increased for URLs in search results having more total appearances of keywords and/or phrases, more clustering of keyword and/or phrases together, or the like. Keywords themselves may be hierarchically ordered, such that each keyword may have a relevance score; a "keyword score" numerical variable for each search result may aggregate keyword scores of keywords from and/or matching search query 140 that are found in contents at the search result. An "inverted index score" may alternatively or additionally generate a score for a search result using the text. A "user history rank" may be calculated based on frequency of past visits to a given search result by a user, which may be tracked, without limitation, in user database 136; frequency of visits by all users in cohort may be so tracked. In an embodiment, two or more of index rank, relevance rank, keyword score, user history rank, and/or inverted score may be aggregated together to calculate a numerical field, vector, or other data object determining an overall rank of a search result. Overall rank, and/or any other component score thereof, may be further weighted by and/or aggregated with, numbers representing one or more additional determinations, such as a detection of problematic content as described below.

Continuing to refer to FIG. 1, computing device 104 is configured to output ranked search result to user. Outputting may include displaying search results in rank order, for instance in the form of a list of links to URLs from search results, each of which a user may select to navigate to web sites and/or other resources at the corresponding URL. In an embodiment, computing device 104 may remove one or more URLs from search results, give the one or more URLs a lower ranking, and/or post a warning message next to such URLs as a result of detection of content that may be problematic to user based on user proclivities and/or behavioral history; this may be performed, without limitation, as described in U.S. Nonprovisional patent Ser. No. 16/673, 673, filed Nov. 4, 2019, and entitled "SYSTEMS AND METHODS FOR CLASSIFYING MEDIA ACCORDING TO USER NEGATIVE PROPENSITIES." Each search result list may be displayed in rank order. Computing device 104 may look up, reconstruct, and/or mark up snippets showing context of matching keywords/phrases.

Still referring to FIG. 1, computing device 104 and/or another device incorporated in and/or in communication with system 100 may be configured to generate physiologically linked web index, or any of indices 116*a-n*. In an embodiment, an index may be generated by modifying ranking information in a general index 144 as a function of a cohort; this may be performed, without limitation, by performing ranking algorithms used for general index 144 limited to a population matching a cohort corresponding to the index to be generated. Alternatively or additionally, computing device 104 and/or other device may produce cohort-specific index by ranking general index 144 entries according to a cohort relevance heuristic 148. Cohort relevance heuristic 148 may include, without limitation, a model that maps keywords to a relevance score, for instance using a linear combination, polynomial combination, or other mathematical expression of keyword identifications and/or frequency of appearance in a web page or other document the output of which is a relevance score. Cohort relevance heuristic 148 may be generated using a machine-learning algorithm and using training data 124 correlating terms with cohort member hits and/or visits to web destinations, which may be anonymously compiled by monitoring navigational choices of cohort member users.

Continuing to refer to FIG. 1, machine learning algorithms used to generate cohort relevance heuristic 148 may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include words extracted from a web destination as described above as inputs, relevance scores as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 124. Persons skilled in the art, upon reviewing the entirety of this disclosure, will be aware of various possible variations of supervised machine learning algorithms that may be used to determine relation between inputs and outputs.

Still referring to FIG. 1, computing device 104 and/or other device may be designed and configured to create a machine-learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis.

Still referring to FIG. 1, heuristic may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 124.

Still referring to FIG. 1, heuristic as described above may be a machine-learning model. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training data set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning In an embodiment, and still referring to FIG. 1, general index 144 entries may be ranked to create cohort-specific index entries by sampling content of listed URLs and applying cohort relevance heuristic 148, alone and/or in combination with other ranking processes, to generate ranking.

Alternatively or additionally, and with continued reference to FIG. 1, generation of cohort specific indices 116a-n may be performed using a web crawler 152. A "web crawler 152," as used in this disclosure, is a program that visits content at URLs and extracts keywords and/or key phrases from content. In an embodiment, web crawler 152 may assess each visited page initially by inspection of a limited number of fields such as <meta> tags, titles, and/or other fields indicative of likely contents, and/or some initial quantity of text received from a site. For instance, a web crawler 152 may check for standard filename robots.txt, addressed to it, which may contains directives for web crawler 152, telling it which pages to crawl. Web crawler 152 may send certain information back to be indexed, such as the titles, page content, JavaScript, Cascading Style Sheets (CSS), headings, or metadata in HTML meta tags. After a certain number of pages crawled, amount of data indexed, or time spent on the website, which may be weighted and/or determined based on heuristic as described in further detail below, web crawler 152 may proceed to a new URL. Web crawler 152 may, without limitation, calculate cohort relevance heuristic 148 using initially analyzed text, and compare resulting score to a threshold, where failing to meet threshold may indicate that content is insufficiently relevant to warrant further analysis. Heuristic output may be combined with output of one or more additional algorithms for determining whether to inspect content at a URL further; for instance relevance score generated using heuristic may be used to weight a relevance score generated by other processes.

In an embodiment, where a feature learning process or the like is used to generate new clusters and/or cohorts, computing device 104 and/or other device may create a new index for each new cohort; new index may be initially populated, without limitation, using entries from indices 116a-n of one or more most proximate cohorts, where proximity may be determined using proximity determination of classifiers and/or feature learning algorithms 128 as described above. Each crawling and/or index generation step and/or process as described above may be performed iteratively, with index entries updated and/or replaced periodically; thus each cohort index may continuously refine its degree of relevance to its corresponding cohort of users.

Figure 4:
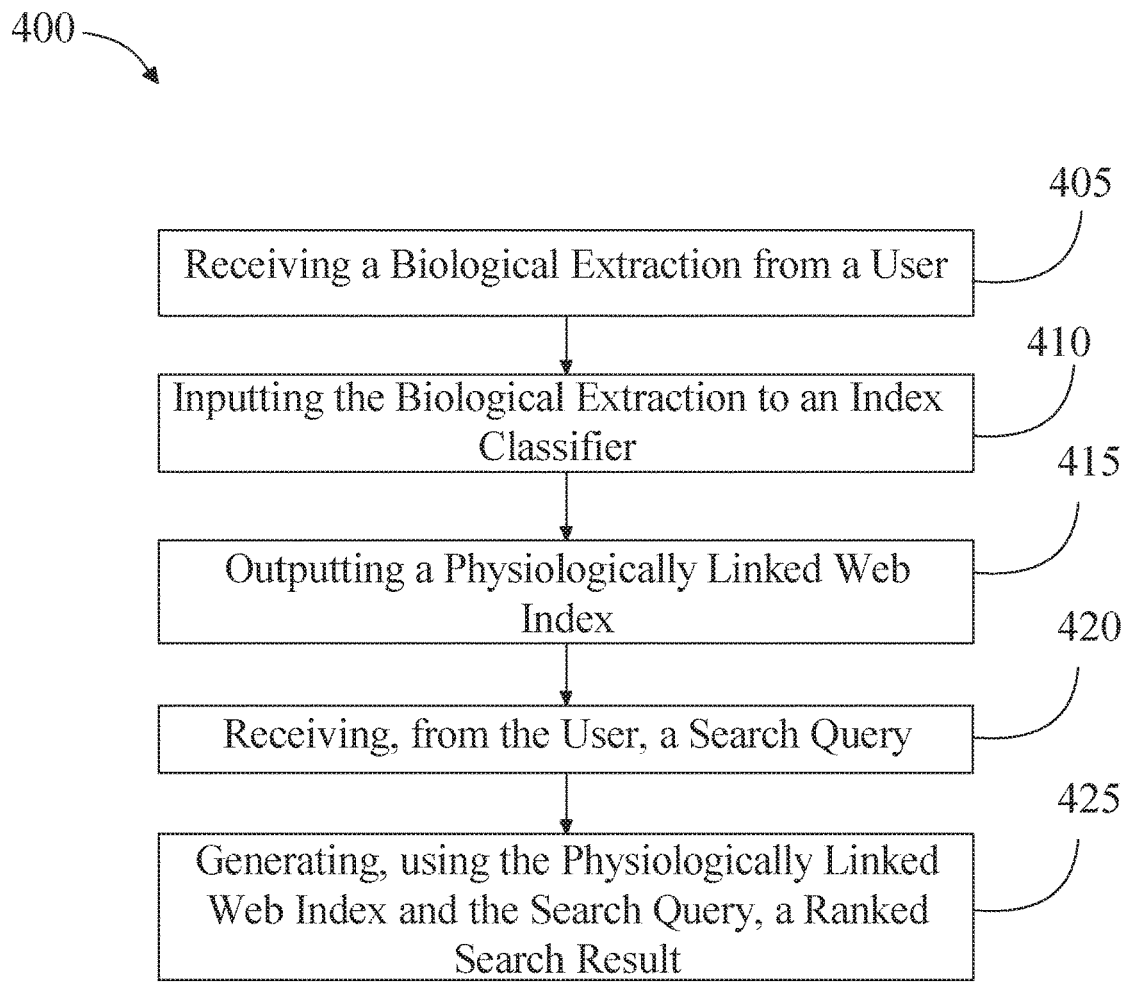
FIG. 4 is a flow diagram illustrating an exemplary embodiment of a method of physiologically informed network searching.

Referring now to FIG. 4, an exemplary embodiment of a method 400 of physiologically informed network searching is illustrated. At step 405, receiving, at a computing device 104, a biological extraction 108 from a user; this may be implemented, without limitation, as described above in reference to FIGS. 1-3. At step 410, inputting, by the computing device 104, the biological extraction 108 to an index classifier 112, the index classifier 112 configured to input biological extractions 108 and output web search indices 116a-n, wherein the classifier is generated by executing a classification algorithm 120 clustering a plurality of user physiological data records to a plurality of user cohort labels; this may be implemented, without limitation, as described above in reference to FIGS. 1-3. For instance, and without limitation, classification algorithm 120 may include a K-nearest neighbors classification algorithm 120. Computing device 104 may generate index classifier 112. Computing device 104 may generate, using a feature learning algorithm 128, the plurality of user cohort labels; the feature learning algorithm 128 may include a k-means clustering algorithm.

At step 415, and still referring to FIG. 4, computing device 104 outputs from the index classifier 112 a physiologically linked web index; this may be implemented, without limitation, as described above in reference to FIGS. 1-3. In an embodiment, computing device 104 generates physiologically linked index 132. Generating physiologically linked index 132 may include modifying a general web index as a function of cohort data. Generating physiologically linked index 132 may include generating the physiologically linked index 132 using a web crawler 152 program. Web crawler 152 program may be configured to evaluate web page relevance using a cohort relevance heuristic 148.

At step 420, and continuing to refer to FIG. 4, computing device 104 may receive, from the user, a search query 140; this may be implemented, without limitation, as described above in reference to FIGS. 1-3. At step 425, computing device 104 may generate, using the physiologically linked web index and the search query 140, a ranked search result; this may be implemented, without limitation, as described above in reference to FIGS. 1-3.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
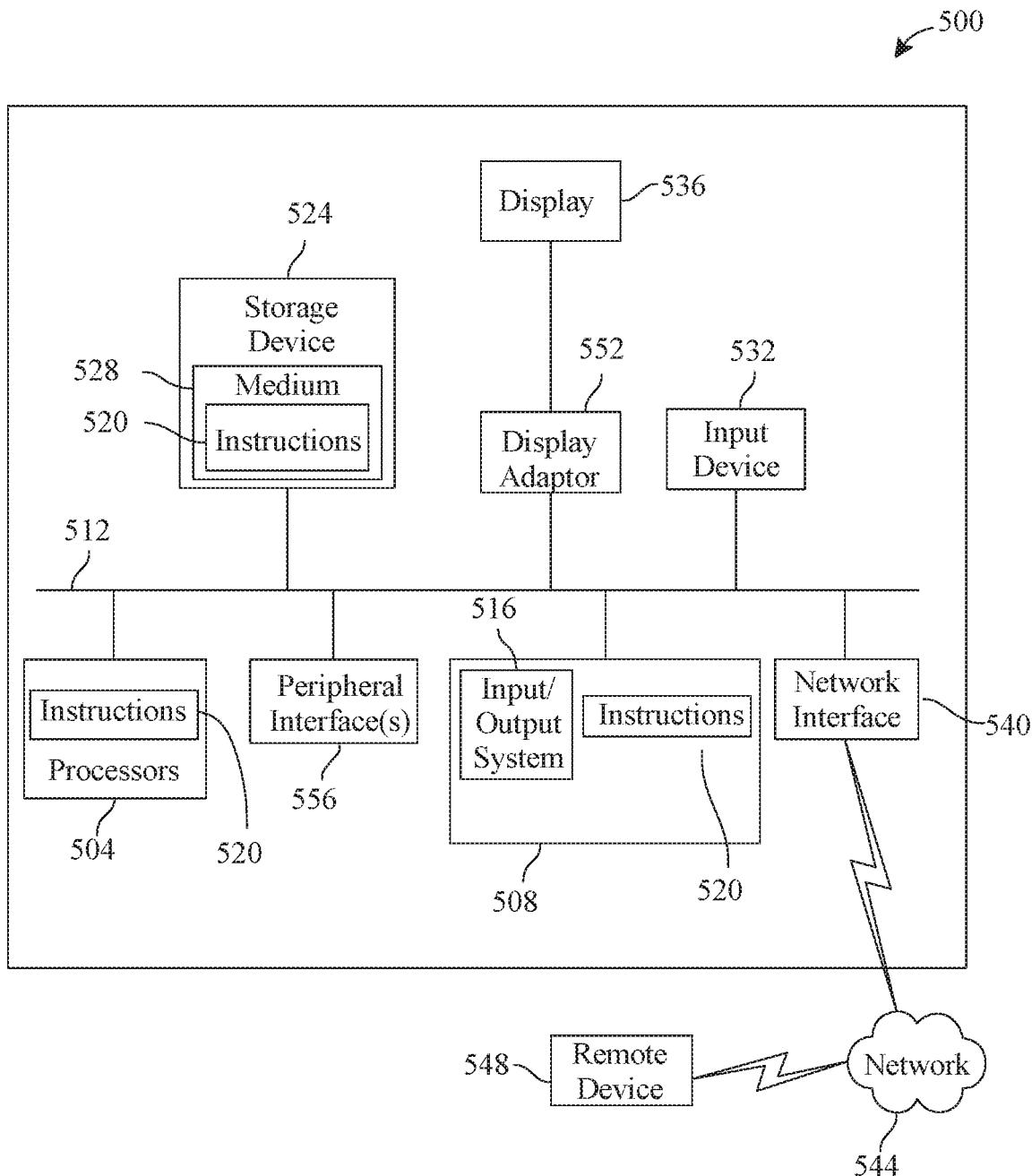
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for physiologically informed network searching, the system comprising a computing device designed and configured to:
   receive a biological extraction from a user;
   generate a cohort-specific index classifier, wherein the index classifier comprises a machine-learning model trained by training data comprising a plurality of user physiological data records and a plurality of user cohort labels configured to receive biological extractions as inputs and output web search indices, the cohort-specific index classifier further comprising a classification algorithm configured to:
   cluster a plurality of user physiological data records to a plurality of user cohort labels, wherein:
      the plurality of user cohort labels is created using a feature learning algorithm configured to detect co-occurrences of sets of physiological data by:
         dividing physiological data from a given user into a plurality of sub-combinations to create a plurality of physiological data sets using a cluster analysis configured to:
            generate an initial set of user cohort labels from an initial set of user physiological data of a plurality of users; and
            iteratively identify new clusters to generate new user cohort labels, wherein the physiological data is classified as a function of the generated new user cohort labels;
         evaluating which physiological data sets tend to co-occur with which other physiological data sets as a function of a degree of a similarity index value;
      each user cohort label from the plurality of user cohort labels is correlated to the plurality of physiological data having a greatest degree of similarity to the biological extraction from the user; and
   rank the web search indices as a function of a cohort relevance heuristic;
output, from the cohort-specific index classifier, a physiologically linked web index, wherein the physiologically linked web index further comprises physiological data of past biological extractions of the user;
receive, from the user, a search query;
determine at least a hidden state as a function of the search query, wherein determining the hidden state comprises:
   parsing the search query into sequential tokens;
   generating a hidden state model of at least a chain of tokens; and
   determining the at least a hidden state as a function of the at least a hidden state model;
generate, using the physiologically linked web index, the at least a hidden state and the search query, a ranked search result, wherein the ranking is determined by:
   calculating an overall rank by aggregating a relevance rank, a keyword score, a user history rank, and an inverted index score; and
   applying a weight factor to the overall rank;
receive, from the user, the user's phenotype, wherein the user's phenotype comprises the user's behavioral history; and
remove, as a function of the user's behavioral history, specific search results from the previously generated ranked search results.

2. The system of claim 1, wherein the classification algorithm further comprises a K-nearest neighbors classification algorithm.

3. The system of claim 1, wherein the computing device is further configured to generate the index classifier.

4. The system of claim 1, wherein the feature learning algorithm further comprises a k-means clustering algorithm.

5. The system of claim 1, wherein the computing device is further configured to generate a physiologically linked index.

6. The system of claim 5, wherein generating the physiologically linked index further comprises modifying a general web index as a function of cohort data.

7. The method of claim 5, wherein generating the physiologically linked index further comprises generating the physiologically linked index using a web crawler program.

8. The method of claim 7, wherein the web crawler program is further configured to evaluate web page relevance using a cohort relevance heuristic.

9. The system of claim 8, wherein the computing device is further configured to generate the cohort relevance heuristic using a supervised machine-learning process.

10. A method of physiologically informed network searching, the method comprising:
receiving, at a computing device, a biological extraction from a user;
generating, by the computing device, a cohort-specific index classifier, wherein the index classifier comprises a machine-learning model trained by training data comprising a plurality of user physiological data records and a plurality of user cohort labels configured to receive biological extractions as inputs and output web search indices, the cohort-specific index classifier further comprising a classification algorithm for:
   clustering a plurality of user physiological data records to a plurality of user cohort labels, wherein:
      the plurality of user cohort labels is created using a feature learning algorithm configured to detect co-occurrences of sets of physiological data by:
         dividing physiological data from a given user into a plurality of sub-combinations to create a plurality of physiological data sets using a cluster analysis configured to:
            generate an initial set of user cohort labels from an initial set of user physiological data of a plurality of users; and
            iteratively identify new clusters to generate new user cohort labels, wherein the physiological data is classified as a function of the generated new user cohort labels;
         evaluating which physiological data sets tend to co-occur with which other physiological data sets as a function of a degree of similarity index value;
      each user cohort label from the plurality of user cohort labels is correlated to the plurality of physiological data having a greatest degree of similarity to the biological extraction from the user; and
   ranking the web search indices as a function of a cohort relevance heuristic;
outputting, by the computing device and from the cohort-specific index classifier, a physiologically linked web index, wherein the physiologically linked web index further comprises physiological data of past biological extractions of the user;
receiving, from the user, a search query;
determining, by the computing device, at least a hidden state as a function of the search query, wherein determining the at least a hidden state comprises:
   parsing the search query into sequential tokens;
   generating a hidden state model of at least a chain of tokens; and
   determining the at least a hidden state as a function of the hidden state model;
generating, using the physiologically linked web index, the at least a hidden state and the search query, a ranked search result, wherein the ranking is determined by:

calculating an overall rank by aggregating a relevance rank, a keyword score, a user history rank, and an inverted index score; and applying a weight factor to the overall rank;

receiving, from the user, the user's phenotype, wherein the user's phenotype comprises the user's behavioral history; and removing, as a function of the user's behavioral history, specific search results from the previously generated ranked search results.

11. The method of claim 10, wherein the classification algorithm further comprises a K-nearest neighbors classification algorithm.

12. The method of claim 10 further comprising generating the index classifier.

13. The method of claim 10, wherein the feature learning algorithm further comprises a k-means clustering algorithm.

14. The method of claim 10 further comprising generating a physiologically linked index.

15. The method of claim 14, wherein generating the physiologically linked index further comprises modifying a general web index as a function of cohort data.

16. The method of claim 14, wherein generating the physiologically linked index further comprises generating the physiologically linked index using a web crawler program.

17. The method of claim 16, wherein the web crawler program is further configured to evaluate web page relevance using a cohort relevance heuristic.

18. The system of claim 1, wherein the physiological data of past biological extractions of the user includes at least a mean corpuscular hemoglobin concentration.

* * * * *